(12) United States Patent
Acosta et al.

(10) Patent No.: US 8,740,763 B2
(45) Date of Patent: *Jun. 3, 2014

(54) MULTILUMEN BRACHYTHERAPY BALLOON CATHETER

(71) Applicant: Hologic, Inc., Bedford, MA (US)

(72) Inventors: George M. Acosta, Menifee, CA (US); Paul Lubock, Monarch Beach, CA (US)

(73) Assignee: Hologic Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/750,596

(22) Filed: Jan. 25, 2013

(65) Prior Publication Data

US 2013/0144105 A1 Jun. 6, 2013

Related U.S. Application Data

(63) Continuation of application No. 12/321,286, filed on Jan. 20, 2009, now Pat. No. 8,360,950.

(60) Provisional application No. 61/062,179, filed on Jan. 24, 2008.

(51) Int. Cl.
*A61N 5/00* (2006.01)

(52) U.S. Cl.
USPC .......................................................... 600/3

(58) Field of Classification Search
USPC ...................................................... 600/1–8
See application file for complete search history.

(56) References Cited

U.S. PATENT DOCUMENTS

| | | | |
|---|---|---|---|
| 3,324,847 A | 6/1967 | Zoumboulis | |
| 3,872,856 A | 3/1975 | Clayton | |
| 3,975,350 A | 8/1976 | Hudgin et al. | |
| 4,119,094 A | 10/1978 | Micklus et al. | |
| 4,454,106 A | 6/1984 | Gansow et al. | |
| 4,571,241 A | 2/1986 | Christopher | |

(Continued)

FOREIGN PATENT DOCUMENTS

| | | |
|---|---|---|
| EP | 0536440 A1 | 4/1993 |
| EP | 0642766 A2 | 3/1995 |

(Continued)

OTHER PUBLICATIONS

*SenoRX, Inc. v. Hologic, Inc.*; District Court for the District of Delaware, Case No. 1:12-cv-00173-LPS-CJB, Complaint filed Feb. 10, 2012.

(Continued)

*Primary Examiner* — Christine Matthews (57) ABSTRACT

The disclosure describes a device for asymmetrical irradiation of a body cavity or site, such as after removal of tissue, e.g. biopsy or lumpectomy. The device includes an elongated tubular shaft having an inner lumen and a tubular wall with a plurality of lumens extending within the wall which are configured for receiving a radiation source. The distal portion of the tubular shaft is cut into a plurality of longitudinally separated wall segments with a lumen extending within at least one of the wall segments. A support member is positioned within the separated wall segments to support and position the wall segments in a desired configuration for brachytherapy. An expandable member such as an inflatable balloon is mounted on the distal shaft portion about the separated wall segments wall which when inflated secures the distal shaft portion within a desired intracorporeal site for brachytherapy treatment.

16 Claims, 8 Drawing Sheets

(56) References Cited

U.S. PATENT DOCUMENTS

| | | |
|---|---|---|
| 4,690,677 A | 9/1987 | Erb |
| 4,763,642 A | 8/1988 | Horowitz |
| 4,929,470 A | 5/1990 | Rittenhouse et al. |
| 4,998,917 A | 3/1991 | Gaiser |
| 4,998,930 A | 3/1991 | Lundahl |
| 5,059,166 A | 10/1991 | Fischell et al. |
| 5,106,360 A | 4/1992 | Ishiwara et al. |
| 5,167,622 A | 12/1992 | Muto |
| 5,199,939 A | 4/1993 | Dake et al. |
| 5,227,969 A | 7/1993 | Waggener et al. |
| 5,259,847 A | 11/1993 | Trambert |
| 5,302,168 A | 4/1994 | Hess |
| 5,312,356 A | 5/1994 | Engelson et al. |
| 5,314,518 A | 5/1994 | Ito et al. |
| 5,336,178 A | 8/1994 | Kaplan et al. |
| 5,342,305 A | 8/1994 | Shonk |
| 5,381,504 A | 1/1995 | Novack et al. |
| 5,411,466 A | 5/1995 | Hess |
| 5,417,687 A | 5/1995 | Nardella et al. |
| 5,428,658 A | 6/1995 | Oettinger et al. |
| 5,429,582 A | 7/1995 | Williams |
| 5,503,613 A | 4/1996 | Weinberger |
| 5,535,817 A | 7/1996 | Dunne |
| 5,566,221 A | 10/1996 | Smith et al. |
| 5,603,991 A | 2/1997 | Kupiecki et al. |
| 5,611,767 A | 3/1997 | Williams |
| 5,616,114 A | 4/1997 | Thornton et al. |
| 5,621,780 A | 4/1997 | Smith et al. |
| 5,624,395 A | 4/1997 | Mikhail et al. |
| 5,653,683 A | 8/1997 | D'Andrea |
| 5,662,580 A | 9/1997 | Bradshaw et al. |
| 5,704,926 A | 1/1998 | Sutton |
| 5,720,717 A | 2/1998 | D'Andrea |
| 5,759,173 A | 6/1998 | Preissman et al. |
| 5,782,742 A | 7/1998 | Crocker et al. |
| 5,820,594 A | 10/1998 | Fontirroche et al. |
| 5,820,717 A | 10/1998 | Siegenthaler |
| 5,863,284 A | 1/1999 | Klein |
| 5,863,285 A | 1/1999 | Coletti |
| 5,899,882 A | 5/1999 | Waksman et al. |
| 5,908,406 A | 6/1999 | Ostapchenko et al. |
| 5,913,813 A | 6/1999 | Williams et al. |
| 5,916,143 A | 6/1999 | Apple et al. |
| 5,919,473 A | 7/1999 | Elkhoury |
| 5,924,973 A | 7/1999 | Weinberger |
| 5,931,774 A | 8/1999 | Williams et al. |
| 5,935,098 A | 8/1999 | Blaisdell et al. |
| 5,993,972 A | 11/1999 | Reich et al. |
| 6,022,308 A | 2/2000 | Williams |
| 6,033,357 A | 3/2000 | Ciezki et al. |
| 6,036,631 A | 3/2000 | McGrath et al. |
| 6,083,148 A | 7/2000 | Williams |
| 6,086,970 A | 7/2000 | Ren |
| 6,093,142 A | 7/2000 | Ciamacco, Jr. |
| 6,095,966 A | 8/2000 | Chornenky et al. |
| 6,143,013 A | 11/2000 | Samson et al. |
| 6,200,257 B1 | 3/2001 | Winkler |
| 6,217,565 B1 | 4/2001 | Cohen |
| 6,251,059 B1 | 6/2001 | Apple et al. |
| 6,256,529 B1 | 7/2001 | Holupka et al. |
| 6,282,142 B1 | 8/2001 | Miyawaki |
| 6,306,074 B1 | 10/2001 | Waksman et al. |
| 6,319,188 B1 | 11/2001 | Lovoi |
| 6,378,137 B1 | 4/2002 | Hassan et al. |
| 6,390,967 B1 | 5/2002 | Forman et al. |
| 6,390,968 B1 | 5/2002 | Harmon |
| 6,390,992 B1 | 5/2002 | Morris et al. |
| 6,398,708 B1 | 6/2002 | Hastings et al. |
| 6,413,203 B1 | 7/2002 | Sahatjian |
| 6,413,204 B1 | 7/2002 | Winkler et al. |
| 6,416,492 B1 | 7/2002 | Nielson |
| 6,458,069 B1 | 10/2002 | Tam et al. |
| 6,482,142 B1 | 11/2002 | Winkler et al. |
| 6,512,942 B1 | 1/2003 | Burdette et al. |
| 6,527,693 B2 | 3/2003 | Munro, III et al. |
| 6,540,655 B1 | 4/2003 | Chin et al. |
| 6,605,030 B2 | 8/2003 | Weinberger |
| 6,610,013 B1 | 8/2003 | Fenster et al. |
| 6,615,070 B2 | 9/2003 | Lee |
| 6,673,006 B2 | 1/2004 | Winkler |
| 6,706,014 B2 | 3/2004 | Banik et al. |
| 6,723,052 B2 | 4/2004 | Mills |
| 6,746,392 B2 | 6/2004 | Stiger et al. |
| 6,752,752 B2 | 6/2004 | Geitz |
| 6,770,058 B1 | 8/2004 | Liprie |
| 6,913,600 B2 | 7/2005 | Valley et al. |
| 6,923,754 B2 | 8/2005 | Lubock |
| 6,955,641 B2 | 10/2005 | Lubock |
| 6,983,754 B1 | 1/2006 | Anderson et al. |
| 7,098,463 B2 | 8/2006 | Adamovics |
| 7,107,089 B2 | 9/2006 | Lee |
| 7,171,255 B2 | 1/2007 | Holupka et al. |
| 7,201,715 B2 | 4/2007 | Burdette et al. |
| 7,214,178 B2 | 5/2007 | Lubock |
| 7,322,929 B2 | 1/2008 | Lovoi |
| 7,404,791 B2 | 7/2008 | Linares et al. |
| 7,407,476 B2 | 8/2008 | Lubock et al. |
| 7,413,539 B2 | 8/2008 | Lubock et al. |
| 7,465,268 B2 | 12/2008 | Lubock et al. |
| 7,476,235 B2 | 1/2009 | Diederich et al. |
| 7,497,819 B2 | 3/2009 | White et al. |
| 7,497,820 B2 | 3/2009 | White et al. |
| 7,513,861 B2 | 4/2009 | Klein et al. |
| 7,517,310 B2 | 4/2009 | Lubock et al. |
| 7,662,082 B2 | 2/2010 | White et al. |
| 7,783,006 B2 | 8/2010 | Stewart et al. |
| 7,885,382 B2 | 2/2011 | Stewart et al. |
| 7,887,476 B2 | 2/2011 | Hermann et al. |
| 8,360,950 B2 * | 1/2013 | Acosta et al. ................ 600/3 |
| 2001/0016725 A1 | 8/2001 | Valley et al. |
| 2001/0049464 A1 | 12/2001 | Ganz |
| 2001/0051669 A1 | 12/2001 | McGhee |
| 2002/0045893 A1 | 4/2002 | Lane et al. |
| 2002/0055666 A1 | 5/2002 | Hunter et al. |
| 2002/0095114 A1 | 7/2002 | Palasis |
| 2002/0177804 A1 | 11/2002 | Saab |
| 2003/0144570 A1 | 7/2003 | Hunter et al. |
| 2004/0039437 A1 | 2/2004 | Sparer et al. |
| 2004/0054366 A1 | 3/2004 | Davison et al. |
| 2004/0087827 A1 | 5/2004 | Lubock |
| 2004/0116767 A1 | 6/2004 | Lebovic et al. |
| 2004/0215048 A1 | 10/2004 | Lubock |
| 2004/0260142 A1 | 12/2004 | Lovoi |
| 2005/0061771 A1 | 3/2005 | Murphy |
| 2005/0080313 A1 | 4/2005 | Stewart et al. |
| 2005/0101823 A1 | 5/2005 | Linares et al. |
| 2005/0124843 A1 | 6/2005 | Singh |
| 2005/0182286 A1 | 8/2005 | Lubock |
| 2005/0240073 A1 | 10/2005 | Apffelstaedt et al. |
| 2005/0240074 A1 | 10/2005 | Lubock |
| 2005/0277577 A1 | 12/2005 | Hunter et al. |
| 2006/0020156 A1 | 1/2006 | Shukla |
| 2006/0020256 A1 | 1/2006 | Bell et al. |
| 2006/0100475 A1 | 5/2006 | White et al. |
| 2006/0116546 A1 | 6/2006 | Eng |
| 2006/0136051 A1 | 6/2006 | Furst et al. |
| 2006/0167416 A1 | 7/2006 | Mathis et al. |
| 2006/0173233 A1 | 8/2006 | Lovoi |
| 2006/0173235 A1 | 8/2006 | Lim et al. |
| 2006/0205992 A1 | 9/2006 | Lubock et al. |
| 2007/0005003 A1 | 1/2007 | Patterson et al. |
| 2007/0055144 A1 | 3/2007 | Neustadter et al. |
| 2007/0106108 A1 | 5/2007 | Hermann et al. |
| 2007/0167666 A1 | 7/2007 | Lubock et al. |
| 2007/0167668 A1 | 7/2007 | White et al. |
| 2007/0191667 A1 | 8/2007 | Lubock et al. |
| 2007/0270627 A1 | 11/2007 | Cutrer et al. |
| 2008/0057298 A1 | 3/2008 | Finley |
| 2008/0064915 A1 | 3/2008 | Lubock |
| 2008/0071212 A1 | 3/2008 | Lubock et al. |
| 2008/0086083 A1 | 4/2008 | Towler |
| 2008/0091055 A1 | 4/2008 | Nguyen et al. |
| 2008/0188705 A1 | 8/2008 | Lubock et al. |
| 2008/0221384 A1 | 9/2008 | Chi Sing et al. |

(56) References Cited

U.S. PATENT DOCUMENTS

| | | |
|---|---|---|
| 2008/0221444 A1 | 9/2008 | Ritchie et al. |
| 2008/0228023 A1 | 9/2008 | Jones et al. |
| 2008/0228024 A1 | 9/2008 | Jones et al. |
| 2008/0228025 A1 | 9/2008 | Quick |
| 2008/0228150 A1 | 9/2008 | Jones et al. |
| 2008/0281142 A1 | 11/2008 | Lubock et al. |
| 2008/0281143 A1 | 11/2008 | Lubock et al. |
| 2008/0287801 A1 | 11/2008 | Magnin et al. |
| 2009/0030259 A1 | 1/2009 | Quick |
| 2009/0124845 A1 | 5/2009 | Lubock et al. |
| 2009/0171157 A1 | 7/2009 | Diederich et al. |
| 2009/0188098 A1 | 7/2009 | Acosta et al. |
| 2009/0198095 A1 | 8/2009 | Acosta et al. |
| 2009/0209805 A1 | 8/2009 | Lubock et al. |
| 2010/0010287 A1 | 1/2010 | Lubock |
| 2010/0048979 A1 | 2/2010 | Jones et al. |
| 2011/0040139 A1 | 2/2011 | Jones et al. |

FOREIGN PATENT DOCUMENTS

| | | |
|---|---|---|
| EP | 0693293 B1 | 1/1996 |
| EP | 0719571 A2 | 7/1996 |
| EP | 0853957 B1 | 7/1998 |
| EP | 0867200 A2 | 9/1998 |
| EP | 1051990 A1 | 11/2000 |
| EP | 1070514 A1 | 1/2001 |
| EP | 1402922 A1 | 3/2004 |
| EP | 1541188 A1 | 6/2005 |
| EP | 1618924 A1 | 1/2006 |
| JP | 10137250 A | 5/1998 |
| JP | 2001120561 A | 5/2001 |
| RU | 2177350 C2 | 12/2001 |
| WO | 9520241 A1 | 7/1995 |
| WO | 9712540 A1 | 4/1997 |
| WO | 9745053 A2 | 12/1997 |
| WO | 9815315 A1 | 4/1998 |
| WO | 9934869 A1 | 7/1999 |
| WO | 0114011 A1 | 3/2001 |
| WO | 0143826 A1 | 6/2001 |
| WO | 0158346 A1 | 8/2001 |
| WO | 0209599 A2 | 2/2002 |
| WO | 02069862 A1 | 9/2002 |
| WO | 2004043531 A1 | 5/2004 |
| WO | 2005037363 A1 | 5/2005 |
| WO | 2005039655 A1 | 5/2005 |
| WO | 2005039665 A1 | 5/2005 |
| WO | 2005067442 A2 | 7/2005 |
| WO | 2007027831 A1 | 3/2007 |
| WO | 2007143560 A2 | 12/2007 |

OTHER PUBLICATIONS

*SenoRX, Inc. v. Hologic, Inc.*; District Court for the District of Delaware, Case No. 1:12-cv-00173-LPS-CJB, Hologic, Inc.'s Answer to Complaint and Counterclaim filed on May 23, 2012.
*SenoRX, Inc. v. Hologic, Inc.*; District Court for the District of Delaware, Case No. 1:12-cv-00173-LPS-CJB, SenoRX's Answer to Counterclaim filed on Jun. 18, 2012.
*SenoRX, Inc. v. Hologic, Inc.*; District Court for the District of Delaware, Case No. 1:12-cv-00173-LPS-CJB, Joint Claim Construction Chart, filed Nov. 16, 2012.
Paul V. Harper, "Some Therapeutic Applications of Radioisotopes", Journal of the Mississippi State Medical Association, Oct. 1966, vol. VII, pp. 526-533.
"Variable shield for radiation-therapy source wire and centering catheter", Research disclosure, Mason Publications, Hampshire, GB, vol. 438, No. 48, Oct. 2000, XP007126916.
Gregory K. Edmundson, et al., "Dosimetric Characteristics of the Mammosite RTS, a New Breast Brachytherapy Applicator", Int. J. Radiation Oncology Biol. Phys, vol. 52, No. 4, pp. 1132-1139, 2002.
Melvin A. Astrahan, PhD et al., "Optimization of Mammosite therapy", Int. J. Radiation Oncology Biol. Phys, vol. 58, No. 1, pp. 220-232, 2004.

Philip H. Gutin, et al., "A coaxial catheter system for afterloading radioactive sources for the interstitial irradiation of brain tumors", J. Neurosur, vol. 56, pp. 734-735, 1982.
R.D. Ashpole et al., "A New Technique of Brachytherapy for Malignant Gliomas with Caesium-137; A New Method Utilizing a Remote Afterloading system", Clinical Oncology, (1990).
Abstracts of the 11th International Conference on Brain tumor Research and Therapy Oct. 31-Nov. 3, 1995, Silverado Country Club and Resort, Napa, California, Journal of Neuro-Oncology 28:72, 1996.
Johannesen, T.B. et al, "Intracavity Fractioned Balloon Brachytherapy in Glioblastoma", Acta Neurochir (Wien) (1999) 141: 127-133.
Xu, Z., et al., "Calculation of Dose Distribution Near an Innovative Concentric Balloon Catheter for Endovascular Brachytherapy", Cardiovascular Radiation Medicine 2, 2000, pp. 26-31, Elsevier Science Inc.
Stubbs, J. B., et al., "Preclinical Evaluation of a Novel Device for Delivering Brachytherapy to the Margins of Resected Brain Tumor Cavities", J. Neurosurg 96, Feb. 2002, pp. 335-343, vol. 96.
Das, R. K., et al., "3D-CT-Based High-Dose-Rate Breast Brachytherapy Implants: Treatment Planning and Quality Assurance", Int. J. Radiation Oncology Biol. Phys. 2004, pp. 1224-1228, vol. 59, No. 4, Elsevier Inc.
*Hologic, Inc., Cytyc Corp., and Hologic L.P. v. Senorx, Inc*; .; Northern District of California, San Jose Division, Case No. 08-CV-0133 RMW, Defendant Senorx, Inc.'s Notice of Motion and Motion for Summary Udgment of Invalidity ('142 Patent, Claims 1 & 8) and Non-Infringement ('813 Patent, Claims 11 & 12; '204 Patent, Claims 4 & 17), filed May 20, 2009, pp. 7-22, discussing Ashpole, et al., "A New Technique of Brachytherapy for Malignant Gilomas with Caesium-137: A New Method for Utilizing a Remote Afterloading System", Clinical Oncology, 1990, pp. 333-336.
Cuttino, L. W., et al., "CT-Guided Multi-Catheter Insertion Technique for Partial Breast Brachytherapy: Reliable Target Coverage And Dose Homogeneity", Brachytherapy 4, 2005, pp. 10-17, Elsevier.
Glasgow, G. P., et al. "Remote Afterloading Technology", AAPM Report No. 41, 1993, pp. i-vi and 1-107, American Institute of Physics, Inc.
Hoshino, T., "Brain Tumor Research Center", Abstracts of the 11th Conference On Brain Tumor Research and Therapy, Journal Of Neuro-Oncology 28, 1996, pp. 31-113.
Tanderup, et al, "Multi-Channel Intracavitary Vaginal Brachytherapy Using Three-Dimensional Optimization of Source Geometry", Radiation & Oncology Journal of the European Society for Therapeutic Radiology and Oncology, 2004, pp. 81-85, Radiotherapy and Oncology 70 (2004), Elsevier Ireland Ltd.
Devic, et al., "Advantages of Inflatable Multichannel Endorectal Applicator in the Neo-Adjuvant Treatment of Patients With Locally Advanced Rectal Cancer With HDR Brachytherapy", Journal of Applied Clinical Medical Physics, Spring 2005, pp. 44-49, vol. 6, No. 2.
Symon, et al. "Individual Fraction Optimization vs. First Fraction Optimization for Multichannel Applicator Vaginal Cuff High-Dose-Rate Brachytherapy", pp. 211-215, Brachytherapy 5 (2006), Elsevier.
Friedman, M, et al., "A New Technic for the Radium Treatment of Carcinoma of the Bladder", Presented at the Thirty-fourth Annual Meeting of the Radiological Society of North America, Dec. 5-10, 1948, pp. 342-362.
Walton, R. J., "Therapeutic Uses of Radioactive Isotopes in the Royal Cancer Hospital", The British Journal of Radiology, 1950, pp. 559-599, William Heinemann, Publisher.
Low-Beer, B. V. A., "Radioisotope Therapy", "The Clinical Use of Radioactive Isotopes" 1950, pp. 284-349, Charles C. Thomas, Publisher, Springfield, Illinois, U.S.A., See pp. 343-349.
Low-Beer, B. V. A., "The Therapeutic Use of Radioactive Isotopes", "Practical Therapeutics", Dec. 1954, pp. 69-87, vol. X, No. 6.
Muller, J. H., "Radiotherapy of Bladder Cancer by Means of Rubber Balloons Filled In Situ With solutions of a Radioactive Isotope (56) References Cited

OTHER PUBLICATIONS (Co60)", Cancer, A Journal of the American Cancer Society, Jul.-Aug. 1955, pp. 1035-1043, vol. 8, No. 4, J. B. Lippincott Company, Philidelphia.

Friedman, M, et al., "Irradiation of Carcinoma of the Bladder by a Central Intracavitary Radium or Cobalt 60 Source (The Walter Reed Technique)", Presented at the Annual Meeting of the American Radium Society, 1955, pp. 6-31.

Hewitt, C. B., et al., "Update on Intracavitary Radiation in the Treatment of Bladder Tumors", The Journal of Urology; Official Journal of the American Urological Association, Inc., 1981, pp. 323-325, vol. 126 September, The Williams & Wilkins Co.

Hieshima, G. B., et al. "A Detachable Balloon for Therapeutic Transcatheter Occlusions 1", Technical Notes, Jan. 1981, pp. 227-228, vol. 138.

Russel, A. H., et al, "Intracavitary Irradiation for Carcinoma of the Urinary Bladder: Rationale, Technique, and Preliminary Results", Int. J. Radiation Oncology. Phys., 1984, pp. 215-219, vol. 10, Pergamon Press Ltd.

Yin, W., "Brachtherapy of Carcinoma of the Esophagus in China, 1970-1974 and 1982-1984", Brachytherapy HDR and LDR, May 4-6, 1989, pp. 52-56.

Kaufman, N., "Remote Afterloading Intraluminal Brachytherapy in the Treatment of Rectal, Rectosigmoid, and Anal Cancer: A Feasibility Study", International Journal of Radiation Oncology, Biology, Physics, Sep. 1989, pp. 663-668, vol. 17, Issue 3, Pergamon Press plc.

Wolf, C. D., et al., "A Unique Nasopharynx Brachytherapy Technique", Official Journal of the American Association of Medical Dosimetrists, 1990, pp. 133-136, vol. 15, Issue No. 3., Pergamon Press.

Fowler, J. F., "Brief Summary of Radiobiological Principles in Fractionated Radiotherapy", Seminars in Radiation Oncology, Jan. 1992, pp. 16-21, vol. 2, No. 1, W. B. Saunders Company.

Nag, S, "Modern Techniques of Radiation Therapy for Endometrial Cancer", Clinical Obstetrics and Gynecology, Sep. 1996, pp. 728-744, vol. 39, No. 3, Lippincott-Raven Publishers.

Pernot, M., "Combined Surgery and Brachytherapy in the Treatment of Some Cancers of the Bladder (Partial Cystectomy and Interstitial Iridium—192)", Radiotherapy & Oncology, 1996, pp. 115-120, Elsevier Science Ireland Ltd.

Micheletti, E., et al., "High-Dose-Rate Brachytherapy for Poor-Prognosis, High-Grade Glioma: (Phase II) Preliminary Results", Tumori, 1996, pp. 339-344.

Nag, S., et al., "Perineal Template Interstitial Barchytherapy Salvage for Recurrent Endometrial Adenocarcinoma Metastatic to the Vagina", Necologic Oncology 66, 1997, pp. 16-19, Article No. GO974722, Academic Press.

Nag, S., et al., "Remote Controlled High Dose Rate Brachytherapy", Critical Reviews in Oncology/Hematology 22, 1996, pp. 127-150, Elsevier Science Ireland Ltd.

Sylvester, J., et al., "Interstitial Implantation Techniques in Prostate Cancer" Journal of Surgical Oncology 1997; 66: 65-75, Wiley-Liss, Inc.

Tan, L. T., et al., Radical Radiotherapy for Carcinoma of the Uterine Cervix Using External Beam Radiotherapy and a Single Line Source Brachytherapy Technique: The Clatterbridge Technique, the British Journal of Radiology, 70, date Dec. 1997, pp. 1252-1258.

Kuettel, M. R., et al., "Treatment of Female Urethral Carcinoma in Medically Inoperable Patients Using External Beam Irradiation and High Dose Rate Intracavitary Brachytherapy" the Journal of Urology, May 1997, pp. 1669-1671, vol. 157, The American Urological Association, Inc.

Slevin, N. J., et al., "Intracavitary Radiotherapy Boosting for Nasopharynx Cancer" The British Journal of Radiology, 70, Apr. 1997, pp. 412-414.

Sneed, P, K., et al., Interstitial Brachytherapy Procedures for Brain Tumors, Seminars in Surgical Oncology 1997; 13: 157-166, Wiley-Liss, Inc.

Dempsey, J. F., et al., "Dosimetric Properties of a Novel Brachytherapy Balloon Applicator for the Treatment of Malignant Brain-Tumor Resection-Cavity Margins" Int. J. Radiation Oncology Biol. Phys., May 1998, pp. 421-429, vol. 42, No. 2, Elsevier.

Kolotas, C., et al., "CT Guided Interstitial High Dose Rate Brachytherapy for Recurrent Malignant Gliomas", The British Journal of Radiology, 72, (1999), pp. 805-808.

Demanes, D, J., et al., "The Use and Advantages of a Multichannel Vaginal Cylinder in High-Dose-Rate Brachytherapy", Int. J. Radiation Oncology Biol. Phys., (1999), pp. 211-219, vol. 44, No. 1, Elsevier Science Inc.

Debicki, M. P., et al., "Localized Current Field Hyperthermia in Carcinoma of the Cervix: 3-D Computer Simulation of SAR Distribution", International Journal of Hyperthermia, 1999, pp. 427-440, vol. 15, No. 5.

Garipagaoglu, M, et al., "Geometric and Dosimetric Variations of ICRU Bladder and Rectum Reference Points in Vaginal Cuff Brachytherapy Using Ovoids", Int. J. Radiation Oncology Biol. Phys., 2004, pp. 1607-1615, Elsevier Inc.

Bowsher, W. G., et al., "Update on Urology-Prostate Cancer, 4-Treatment of Local Disease", European Journal of Surgical Oncology, 1995 pp. 679-682, vol. 21, No. 6.

Voung, T, et al., "High-Dose-Rate Endorectal Brachytherapy in the Treatment of Loacally Advanced Rectal Carcinoma: Technical Aspects", Brachytherapy 4, 2005, pp. 230-235, Elsevier.

Harada, T, et al., "Transcystoscopic Intracavitary irradiation for Carcinoma of the Bladder: Technique and Preliminary Clinical Results", The Journal of Urology, Oct. 1987, pp. 771-774, vol. 138, No. 4, The Williams & Wilkins Co.

Hall, J. W., et al., "Histologic Changes in Squamous-Cell Carcinoma of the Mouth and Oropharynx Produced by Fractionated External Roentgen Irradiation", Radiological Society of North America, 1948, pp. 318-350, 50/3/MAR.

Hine, G. J., et al., "Isodose Measurements of Linear Radium Sources in Air and Water by Means of an Automatic Isodose Recorder",The American Journal of Roentgenology and Radium Therapy, 1950, pp. 989-998, vol. 64, No. 6, The Societies.

Walton, R. J., et al., Radioactive Solution (24Na and 82 Br) in the Treatment of Carcinoma of the Bladder:, British Medical Bulletin, 1952, pp. 158-165, Medical Dept., The British Council.

Marshall V. F., et al., "Current Clinical Problems Regarding Bladder Tumors", Symposium on Bladder Tumors, 1956, pp. 543-550, 9/3/May-Jun, J. B. Lippincott Co, Etc.

Hewitt, C. B., et al., "Intracavitary Radiation in the Treatment of Bladder Tumors", The Journal of Urology, vol. 107, Apr. 1972, pp. 603-606, The Williams & Wilkins Co.

Rotman, M., et al., "The Intracavitary Applicator in Relation to Complications of Pelvic Radiation—The Ernst System", Int. J. Radiation Oncology Biol. Phys., 1978, pp. 951-956, vol. 4, Pergamon Press Inc.

Nag, S., et al., "The Future of High Dose Rate Brachytherapy", High Dose Rate Brachytherapy: A Textbook, 1994, pp. 447-453, Futura Publishing Company, Inc. , Armonk, New York 10504.

Wang, C. C., "Carcinoma of the Nasopharynx", Radiation Therapy of Head and Neck Neoplasms, 1997, pp. 257-280, Chapter 10, Wiley-Liss, Inc.

Gaspar, L. E., et al., "Esophageal Brachytherapy", Principles and Practice of Brachytherapy, 1997, pp. 305-321, Futrua Publishing Company, Inc., Armouk, New York.

Vicini, F. A., et al, "Dose-Volume Analysis for Quality Assurance of Interstitial Brachytherapy for Breast Cancer", Int. J. Radiation Oncology Biol. Phys., vol. 45, 1999, pp. 803-810, Elsevier Science Inc.

Akagi, Y, et al., "Optimum Fractionation for High-Dose-Rate Endoesophageal Brachytherapy Following External Irradiation of Early State Esophageal Cancer", Int. J. Radiation Oncology Biol. Phys., vol. 43, 1999, pp. 525-530, Elsevier Science, Inc.

XP007904995:retrieved from the internet: URL: http://www2.dupont.com/Teflon__Industrial/en__US/assets/downloads/h88800.pdf; retrieved on Jun. 19, 2008, by Authorized Officer in International Application PCT/US2008/003364.

Lewis, J, et al., "Intracranial Brachytherapy Using a High Dose Rate Microselectron", Northern Centre for Cancer Treatment, Dept. Of Neurosciences, Regional Medical Physics Department, Newcastle (56) References Cited

OTHER PUBLICATIONS

General Hospital, Newcastle Upon Tyne, UK, Radiation and Oncology, vol. 39, Supplement 1, May 1996, pp. 45-45(1).
International Search Report for PCT/US2008/003364 mailed Aug. 27, 2008.
Written Opinion of the International Searching Authority for PCT/US2008/003364 dated Sep. 15, 2009.
International Preliminary Report on Patentability for PCT/US2008/003364 issued Aug. 3, 2010.
International Search Report for PCT/US2008/003217 mailed Aug. 12, 2008.
Written Opinion of the International Searching Authority for PCT/US2008/003217 dated Sep. 12, 2009.
International Preliminary Report on Patentability for PCT/US2008/003217 dated Mar. 21, 2011.
International Search Report for PCT/US03/33775 mailed Jun. 21, 2004.
International Preliminary Report on Patentability for PCT/US03/33775 dated Oct. 10, 2007.
International Search Report for PCT/US2006/044067 mailed Dec. 18, 2007.
Written Opinion of the International Searching Authority for PCT/US2006/044067 dated Jan. 11, 2009.
International Preliminary Report on Patentability for PCT/US2006/044067 dated Oct. 2, 2009.
International Search Report for PCT/US2006/043891 mailed Sep. 25, 2007.
Written Opinion of the International Searching Authority for PCT/US2006/043891 dated May 18, 2008.
International Preliminary Report on Patentability for PCT/US2006/043891 dated Jan. 12, 2009.
International Search Report for PCT/US2009/000402 mailed Apr. 15, 2009.
Office Action dated Feb. 1, 2013 in U.S. Appl. No. 13/571,495.
Office Action dated Mar. 13, 2013 in U.S. Appl. No. 13/649,668.

\* cited by examiner

MULTILUMEN BRACHYTHERAPY BALLOON CATHETER

RELATED APPLICATIONS

This application is a continuation of U.S. application Ser. No. 12/321,286, filed Jan. 20, 2009, which is related to provisional application Ser. No. 61/062,179, filed on Jan. 24, 2008, which are incorporated herein in their entirety and from which priority is claimed.

FIELD OF THE INVENTION

This invention generally relates to devices and methods for treating tissue surrounding a body cavity, such as a site from which cancerous, pre-cancerous, or other tissue has been removed.

BACKGROUND OF THE INVENTION

In diagnosing and treating certain medical conditions, it is often desirable to perform a biopsy, in which a specimen or sample of tissue is removed for pathological examination, tests and analysis. A biopsy typically results in a biopsy cavity occupying the space formerly occupied by the tissue that was removed. As is known, obtaining a tissue sample by biopsy and the subsequent examination are typically employed in the diagnosis of cancers and other malignant tumors, or to confirm that a suspected lesion or tumor is not malignant. Treatment of cancers identified by biopsy may include subsequent removal of tissue surrounding the biopsy site, leaving an enlarged cavity in the patient's body. Cancerous tissue is often treated by application of radiation, by chemotherapy, or by thermal treatment (e.g., local heating, cryogenic therapy, and other treatments to heat, cool, or freeze tissue).

Cancer treatment may be directed to a natural cavity, or to a cavity in a patient's body from which tissue has been removed, typically following removal of cancerous tissue during a biopsy or surgical procedure. For example, U.S. Pat. No. 6,923,754 to Lubock and U.S. patent application Ser. No. 10/849,410 to Lubock, the disclosures of which are all hereby incorporated by reference in their entireties, describe devices for implantation into a cavity resulting from the removal of cancerous tissue which can be used to deliver cancer treatments to surrounding tissue. One form of radiation treatment used to treat cancer near a body cavity remaining following removal of tissue is "brachytherapy" in which a source of radiation is placed near to the site to be treated.

Lubock above describes implantable devices for treating tissue surrounding a cavity left by surgical removal of cancerous or other tissue that includes an inflatable balloon constructed for placement in the cavity. Such devices may be used to apply one or more of radiation therapy, chemotherapy, and thermal therapy to the tissue surrounding the cavity from which the tissue was removed. The device may be configured to receive a solid or a liquid radiation source or both. Radiation treatment is applied to tissue adjacent the balloon of the device by placing radioactive material such as radioactive "seeds" in a delivery lumen within a distal treatment location. Such treatments may be repeated if desired. While the radiation source is typically a solid radiation source, a radiation source such as a miniature or micro-miniature x-ray tube may also be used (e.g. U.S. Pat. No. 6,319,188). The x-ray tubes are small, flexible and are believed to be maneuverable enough to reach the desired treatment location within a patient's body. The radiation source is to be removed following each treatment session, or remains in place as long as the balloon remains within the body cavity. These inflatable treatment delivery devices and systems are useful to treat cancer in tissue adjacent a body cavity.

However, radiation, chemotherapy, thermal treatment, and other cancer treatments often have deleterious effects on healthy tissue in addition to the desired effects on cancerous tissue. In such treatments, care must be taken to direct the maximum treatment effects to diseased tissue while minimizing its delivery or effects on healthy tissue. For example, radiation treatment may be most effective when only the portion of tissue requiring treatment receives the radiation and where surrounding healthy tissue is unaffected. Tissue cavities typically are not uniform or regular in their sizes and shapes, so that differences in dosages applied to different regions of surrounding tissue, including "hot spots" and regions of relatively low dosage, often result from radiation treatment.

Features of a treatment delivery device for treating tissue adjacent a body cavity, included in the Contura™ multilumen balloon catheter, have been disclosed in U.S. Pat. No. 6,923,754. This patent describes applying a partial-vacuum or suction to bring tissue towards an inflated balloon around a radiation source and allows for uniform application of radiation to tissue surrounding a body cavity. Additional features are described in copending application Ser. No. 11/593,784 and Ser. No. 11/593,789 relating to multilumen catheters which allow a greater degree of flexibility in asymmetric radiation source placement within the body cavity. However, some of these catheter constructions are complex and difficult to manufacture.

SUMMARY OF THE INVENTION

This invention is generally directed to a balloon catheter for treating a patient's body cavity or other intracorporeal site (hereinafter collectively referred to as a body cavity) and methods for such treatments. The invention is particularly suitable for treating tissue adjacent to a body cavity formed by the removal of tissue such as from a patient's breast in a lumpectomy.

More specifically, a device embodying features of the invention has an elongated shaft, a distal end, a distal shaft portion which has a treatment location and an inner lumen extending to the distal shaft portion. The elongated shaft has a shaft wall which at least in part defines an inner lumen and which has a plurality of lumens within the wall. The shaft wall in the distal shaft portion has a plurality of separated longitudinal wall segments having at least one lumen extending therein. A support member preferably extends within the distal shaft portion to support the separated longitudinal wall segments and preferably has a plurality of recesses configured to receive and support the separated longitudinal wall segments. The recesses of the support member preferably place the wall segments into a convex arcuate configuration away from a central longitudinal axis. The support member preferably has an inner lumen in fluid communication with the inner lumen defined by the shaft wall and preferably continues and is in fluid communication with the inner lumen of a tubular member within the inner lumen of the elongated shaft. The distal ends of the separated longitudinal wall segments are secured to the distal end of the support member or a distal tip of the elongated shaft with the separated wall segments in convex arcuate configurations away from the longitudinal axis. A distal tip at the distal end of the shaft preferably closes off the inner lumen of the support member and one or more of the lumens which extend within the wall segments.

The inner lumen of the elongated shaft within the treatment location and at least one of the lumens extending within the separated longitudinal wall segments are configured to receive a radiation source so as to treat tissue adjacent to the distal shaft portion. The lumens may be coated with a lubricous material or lined with a tubular member with an inner lumen having suitable lubricous properties (or a lubricous material thereon) to allow radiation sources to be readily advanced therein.

Preferably, the catheter has an enlarged or enlargeable cavity filling member at the treatment location, such as an inflatable which at least in part fills the body cavity. The cavity filling member is mounted onto the distal shaft portion surrounding the separated longitudinal wall segments so that when expanded will hold tissue lining the body cavity in a desired configuration. The proximal end of the balloon is secured proximal to the arcuate separated longitudinal segments and the distal end is secured to the distal ends of the separated longitudinal wall segments, the distal tip or both.

The distal tip of the catheter preferably has proximally extending plugs members to close off the lumens within the wall segments and preferably, the inner lumen of the support member.

One or more of the lumens in the shaft wall may be used to deliver inflation fluid to the interior of a balloon surrounding the distal shaft portion. One or more of the lumens in the shaft wall may be connected to a vacuum source to provide a vacuum to regions surrounding the distal shaft portion proximal and/or distal to the balloon through one or more vacuum ports therein, such as described in U.S. Pat. No. 6,923,754 and co-pending application Ser. No. 10/849,410 filed on May 19, 2004, both of which are assigned to the SenoRx, Inc., present assignee. Application of a vacuum within the inner lumen aspirates fluid in the cavity through one or more vacuum ports and the vacuum within the body cavity pulls tissue defining the cavity onto the exterior of the cavity filling member deployed within the cavity.

The arcuate configuration of the longitudinal wall segments allows for asymmetric deployment of radiation sources within the body cavity as described in co-pending application Ser. No. 11/593,784, and Ser. No. 11/593,789, both filed on Nov. 6, 2006, so as to be closer to a first portion of tissue surrounding the cavity than a second portion of tissue surrounding the cavity opposite the first tissue portion. This facilitates the radiation source to be offset or capable of being offset within the body cavity so that tissue of one portion of the cavity closer to the source receives more intense radiation treatment and tissue of the second portion further from the source receives less radiation.

The elongated shaft may also have one or more radiation shielding components designed to reduce or minimize damaging irradiation of healthy tissue surrounding the body cavity while treating nearby areas having diseased tissue with radiation emitted from the radiation source. The radiation shielding components include one or more radiation shields disposed about a delivery shaft containing the radiation source. Suitable radiation shielding components are describe in co-pending application Ser. Nos. 11/593,678 and 11/593,952, both filed on Nov. 6, 2006, both assigned to SenoRx, Inc. the present assignee.

A method for treating a body cavity or other intracorporeal site of a patient includes delivering a treatment agent such as a radiation source to a body cavity to treat the desired tissue while minimizing damaging irradiation of healthy tissues. More specifically, a method for treating a body cavity or intracorporeal site includes providing a device having an elongate shaft with a proximal end, a distal end, and a treatment location in a distal portion of the shaft. The method further includes providing a radiation source configured to be deposited in the treatment location and a radiation shielding component partially encircling the treatment location which is configured to control at least in part the emission of radiation emitted from the treatment location. The device is advanced within the patient until the treatment location of the device is deployed within the body cavity or site and the radiation source is positioned within the treatment location. The radiation shielding component is positioned to shield portions of the body cavity from radiation emitted from the radiation source.

A patient's skin is susceptible to damage from radiation delivered by isotopes (e.g. seeds) or x-ray catheters in a lumen of a radiation balloon catheter if the radiation source is too close to the skin. Generally, radiation treatments using a radiation balloon catheter is usually not performed on patients where the body cavity (e.g. from a lumpectomy) is less than 5 mm, sometimes less than 7 mm from the patient's skin. Additionally, over inflation of the balloon can thin and stretch the skin. The application of a vacuum to the body cavity can help by pulling the tissue to the balloon and increased cavity to skin surface distances would result. However, in some instances it would still be too thin to treat. The number of potential patient's which are suitable candidates for treatments with the present device is significantly increased due to reducing the potential for skin tissue damage.

The surface (inside or outside) of the balloon or within the balloon wall may be provided with indicator marks for location or orientation detection during the procedures. For example, dots or lines to help place balloon in appropriate position under CT, x-ray or fluoroscopy. The indicator marks may be radiopaque. Alternatively, or additionally, ultrasound indicators or MRI and direct visual indicators could be incorporated. The indicator marks may extend along the catheter shaft to help with placement of the catheter device during the treatment procedure and the orientation of the off-set lumen and shield.

One attractive additional feature for brachytherapy for breast lumpectomy sites is to provide heat to the tissue lining of the cavity either simultaneously with or sequentially to (before or after) irradiation. Suitable means to do this are described in U.S. Pat. No. 5,106,360 (Ishiwara et al.) wherein brachytherapy catheter is provided with heating electrical coils in the treatment region of the catheter. Other means such as inflation fluid at elevated temperatures may be employed. Generally, tissue temperature must be less than 100°, preferably less than 60° C. to avoid excess damage to surrounding health tissue.

The present invention provides a brachytherapy catheter device which is effective, easy to use and which is easy to manufacture. These and other advantages of the present invention are described in more detail in the following written description and the accompanying exemplary drawings.

DETAILED DESCRIPTION OF THE INVENTION

The present invention is directed to devices and methods for treatment of a patient's body cavity, particularly to deliver asymmetrical radiation into a body cavity such as a cavity left after removal of tissue from the site. While the detailed description is directed to a device configured for treating a patient' breast after tissue removal such as in a lumpectomy, other body sites may also be treated with the device.

FIGS. 1-8 illustrate a brachytherapy catheter device 10 embodying features of the invention which has an elongated shaft 11, a distal tip 12, a treatment location 13 in a distal shaft portion 14 proximal to the distal tip. The device 10 has a balloon 15 on the distal shaft portion 14 which surrounds the treatment location 13. A hub 16 is mounted on the proximal end of the shaft 11 which has an inflation line 17 with leur connection 18, a vacuum line 19 with a leur connection 20 and four outer delivery tubes 21, 22, 23, 24 for delivery of a radiation source through the lumens thereof to the treatment location 13 off set from a centrally location longitudinal axis 25 to provide asymmetrical radiation of tissue surrounding the balloon 15. The leur connections 18 and 20 are provided with threaded caps 26 and 27 respectively to close off the connections. Each of the delivery tubes has a removable cap 28, 29, 30, and 31 respectively to close of the delivery tubes until use. A centrally located delivery tube 32 is provided for radiation source delivery along the central longitudinal axis within the treatment location which also has a removable cap 33.

Figure 1:
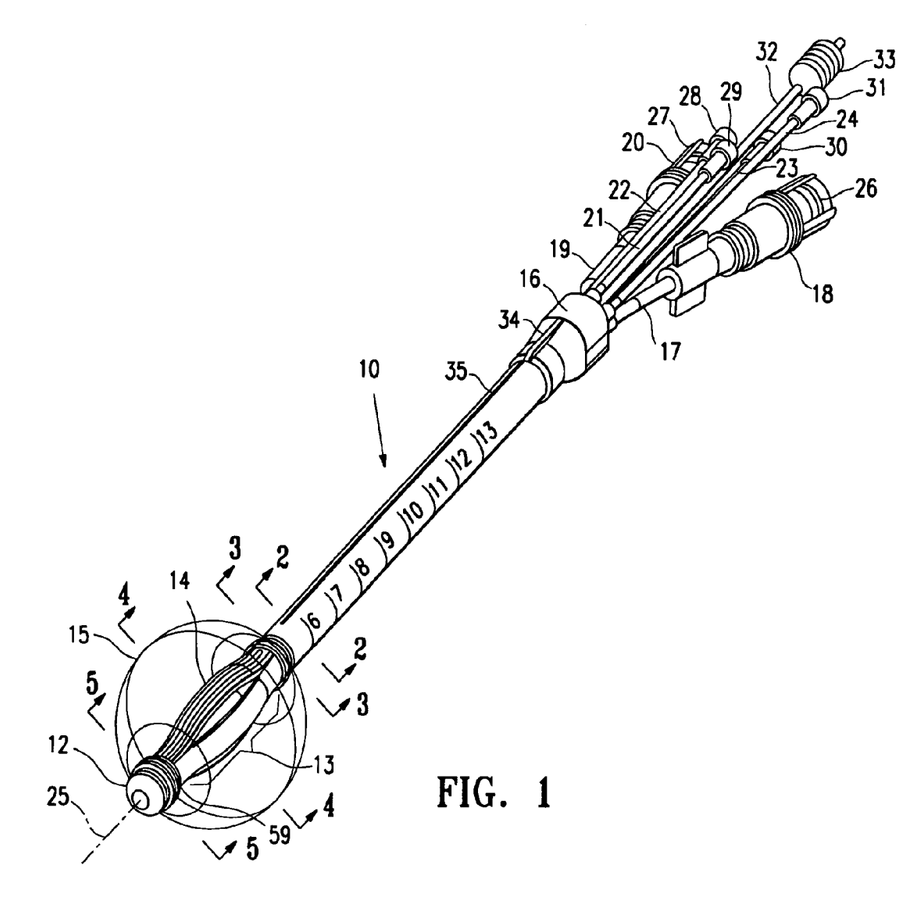
FIG. 1 is a schematic perspective view, partially in section, of a brachytherapy device embodying features of the invention.

The hub 16 has a ridge 34 which is aligned with marker line 35 to provide the physician or other professional the orientation of the treatment location 13. The elongated shaft 11 may also be provided with depth markings to help in the placement of the balloon 15 within the cavity.

Figure 2:
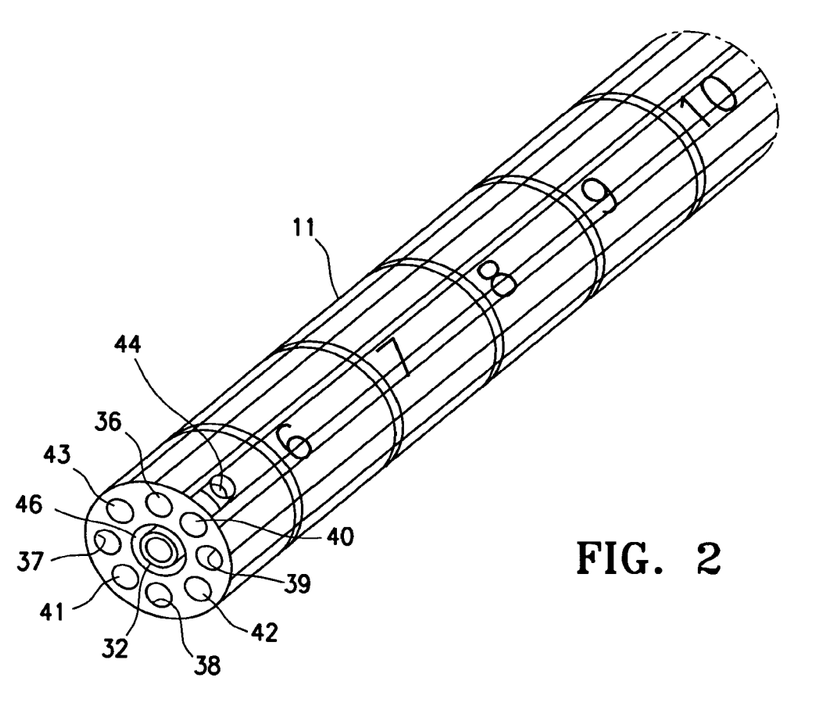
FIG. 2 is a transverse cross sectional view of the device shown in FIG. 1 taken along lines 2-2.
Figure 5:
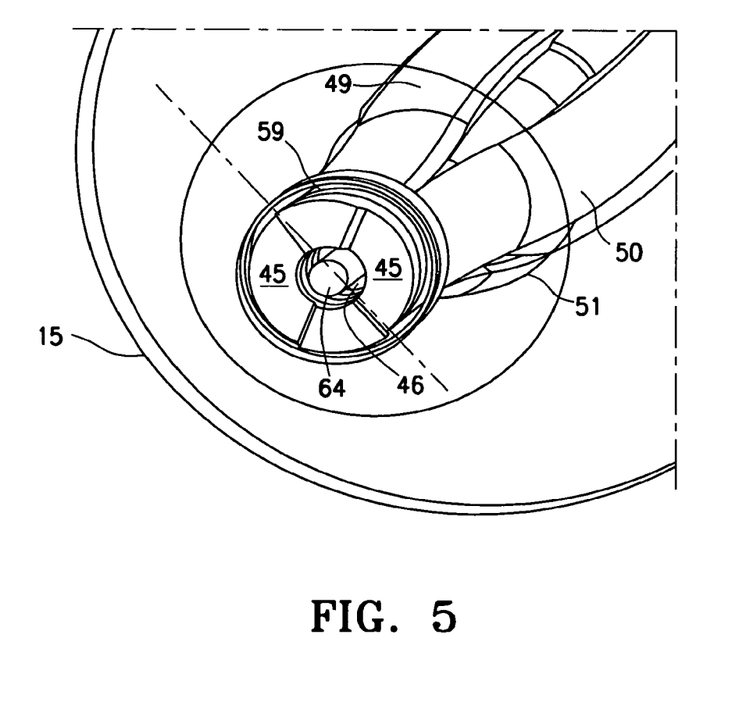
FIG. 5 is a transverse cross sectional view of the device shown in FIG. 1 taken along the lines 5-5.
Figure 6:
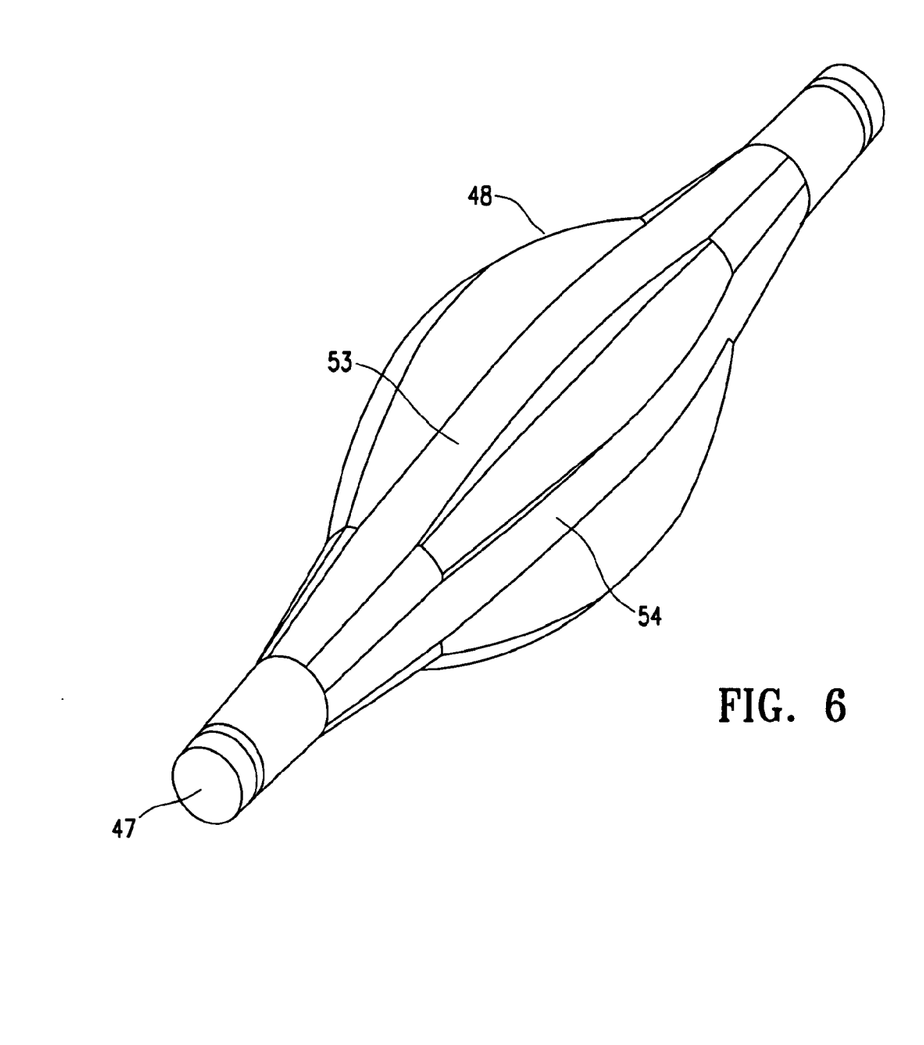
FIG. 6 is a perspective view of the support member in the embodiment shown in FIG. 1.

As shown best in FIG. 2, the elongated shaft 11 has eight lumens, four lumens 36, 37, 38 and 39 equally spaced about the longitudinal axis 25 for radiation source delivery as described above and four equally spaced additional lumens 40, 41, 42 and 43, lumen 40 for vacuum application and lumen 42 for inflation fluid delivery to the interior of balloon 15. Lumens 41 and 44 are not used in this embodiment, but may be used for a variety of functions. A proximal vacuum port 44 is provided in fluid communication with lumen 40 and distal vacuum port 45 (shown best in FIGS. 5 and 7-8) is provided in the distal tip 12 which is in fluid communication with lumen 40 through the annular space 46 between the central delivery tube 32 and center lumen 47 of support member 48 shown in FIGS. 2-4. The support member 48, which is best shown in FIG. 6.

Figure 3:
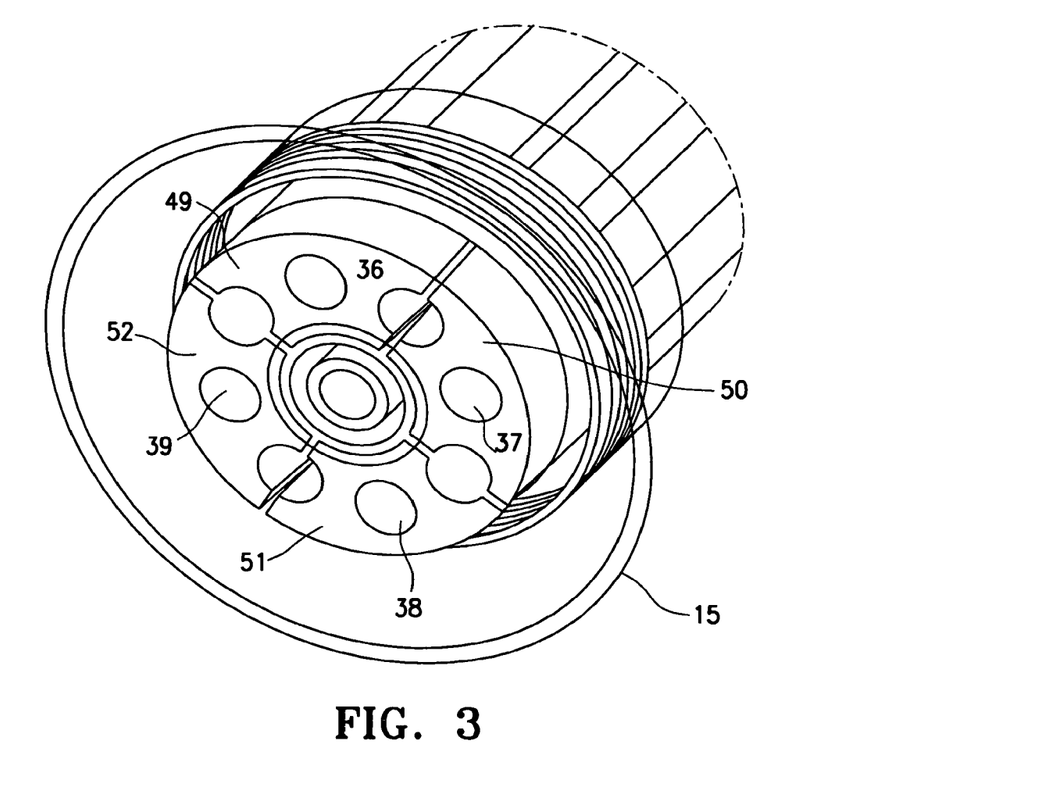
FIG. 3 is a transverse cross sectional view of the device shown in FIG. 1 taken along the lines 3-3.
Figure 4:
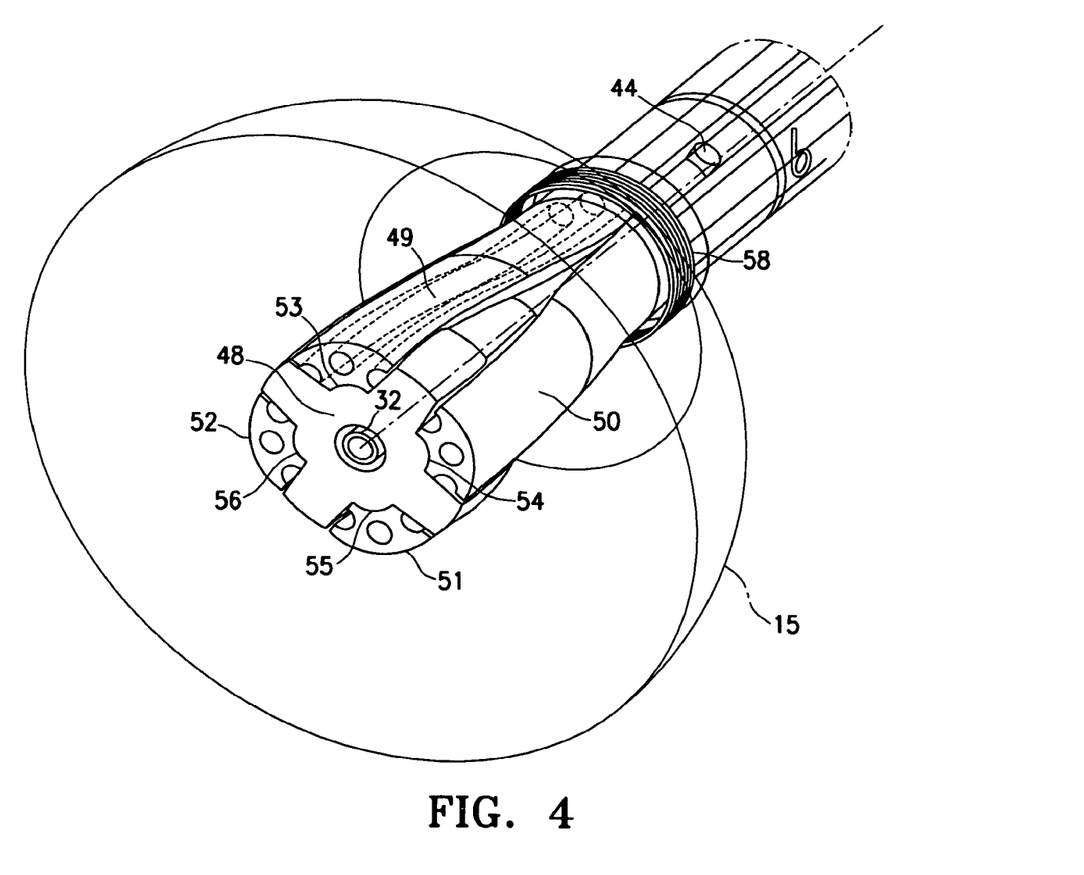
FIG. 4 is a transverse cross sectional view of the device shown in FIG. 1 taken along the lines 4-4.

As shown in FIGS. 1, 3 and 4, the distal shaft portion 14 is split into four separate longitudinal wall segments 49, 50, 51 and 52, with each wall segment having one of the radiation source lumens 36-39 and being disposed within one of the recesses 53-56 in the exterior surface of support member 48. Recesses 55-56 are not shown in FIG. 6 but are on the opposite side of support member 48. The longitudinal wall segments 49-52 are slit through the lumens 40-43 as best shown in FIGS. 3-5. Lumens 40-43 are plugged off proximal to the split of the wall segments 49-52. This wall segment structure facilitates the manufacture of the catheter. The elongated shaft may be extruded with all eight lumens 36-43 in place and the distal shaft portion 14 is segmented by cutting through lumens 40-43 by a cutting blade or other suitable cutting element. The support member 48 may be slid over the central delivery tube 32 with the proximal end of the support member secured within the central lumen of the shaft 11. The free ends of the slit wall segments 49-52 are secured to the distal end of the support member 48. The balloon 15 may then be secured to the shaft 11 with wound sutures 57 and 58 further securing the ends of the balloon to the shaft. The outer delivery tubes 21-24 may extend through lumens 36-39 to the distal ends of the wall segments 49-52. Inflation line 17 and vacuum line 19 may likewise extend through lumens 40 and 41 to a location (not shown) proximal to the split of the wall segments 49-52.

Figure 7:
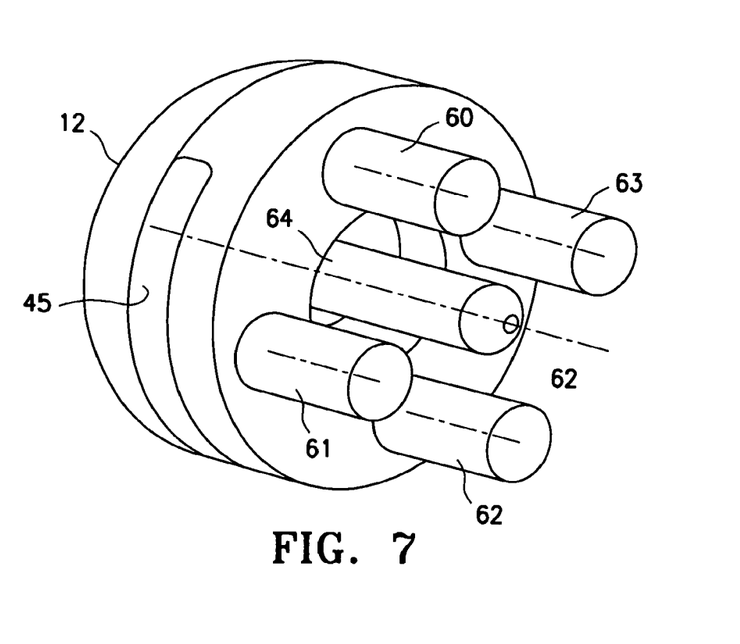
FIG. 7 is a perspective view of the distal tip of the device shown in FIG. 1.
Figure 8:
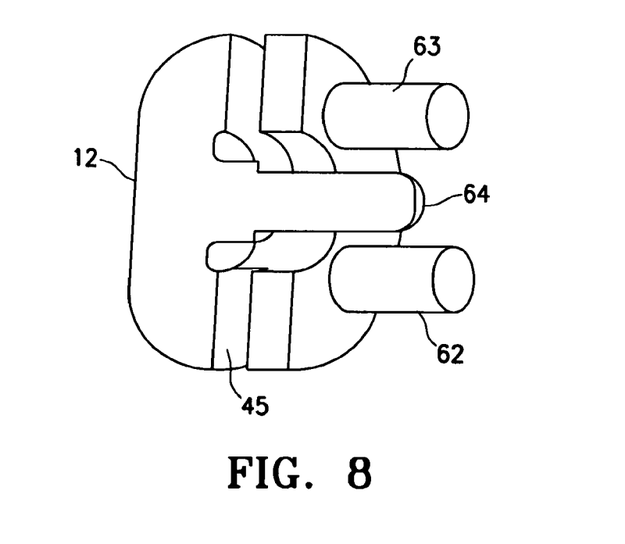
FIG. 8 is a longitudinal cross-sectional view of the distal tip shown in FIG. 7.

As best shown in FIGS. 5, 7 and 8, the distal tip 12 has the distal vacuum port 45 which is in fluid communication with the annular space 46 between central delivery tube 32 and lumen 47 of support member 48. The distal tip 12 is provided with outer source lumen plugs 60-63 for plugging lumens 36-39 and center source lumen plug 64 for plugging the distal end of central tube 32.

The brachytherapy catheter device 10 is readily manufactured. The elongated shaft 11 is extruded, preferably with the lumens 36-43 within the wall and the central lumen 46. The distal shaft portion 14 is cut by a suitable cutting member such as a razor or knife like member to form the plurality of separated longitudinal wall segments 49-52. The support member 48 is preferably machined from an extruded tubular polymeric product to form the recesses 53-56 and overall shape and centrally placed within the separated longitudinal wall segments. A tubular member 32 is positioned within the inner lumen of the elongated shaft 11 and may continue to the distal end of the shaft through the inner lumen of the support member 48. The distal tip 12 is secured to the distal end of the shaft 11 and support member 48 with plug members 60-63 inserted into the lumens within the wall segments 49-52 and central plug member 64 within the lumen of the centrally disposed tubular member 32. The distal tip 12 is preferably preformed with the vacuum ports 45. The distal ends of the separated longitudinal wall segments are secured to the distal end of the device, preferably to the distal end of the support member. The balloon 15 is mounted about the wall segments 49-52 and support member 48 with the distal end of the balloon secured to the distal end of the wall segments and support member and the proximal end of the balloon is secured to the elongated shaft proximal to the separated longitudinal wall segments. Preferably, strands or sutures are wrapped around each of the mounted ends of the balloon 15 to provide further support to the ends. The proximal end of the device 10 is similar to the brachytherapy devices previously described in copending application Ser. Nos. 11/593,784 and 11/593,789 previously referred to herein.

A body cavity within a patient may be treated with the device 10 by inserting the distal shaft portion 13 into the desired body cavity, inflating the balloon 15 with inflation fluid to secure the device within the patient and applying a vacuum to either the distal or proximal vacuum ports or both to conform the tissue lining the cavity to the exterior of balloon 15. A radiation source is advanced through one or more of the source delivery lumens until the radiation source is properly positioned within the treatment location 13 (or prepositioned therein). The radiation source (not shown) is maintained at the treatment location 13 for a prescribe period of time, usually less than 30 minutes and typically a few (5-10) minutes. The radiation source may be placed at several places within the treatment location with within one or multiple source lumens. At the end of the treatment time, the radiation source may be removed from device 10 or the entire device may be withdrawn from the patient. Preferably, the device is left in place so that further radiation treatments may be performed.

The radiation source for the brachytherapy device 10 can include a solid, liquid or slurried radiation source. Suitable liquid radiation sources include, for example, a liquid containing a radioactive iodine isotope (e.g., $I^{125}$ or $I^{131}$), a slurry of a solid isotope, for example, $^{198}$Au or $^{169}$Yb, or a gel containing a radioactive isotope. Liquid radiation sources are also commercially available (e.g., Iotrex®, Proxima Therapeutics, Inc., Alpharetta, Ga.). The solid radiation source may be a radioactive microsphere available from 3M Company of St. Paul, Minn. A micro miniature x-ray source may also be utilized. The radiation source may be either preloaded into the device 10 at the time of manufacture or may be loaded into the device 10 before or after placement into a body cavity or other site of a patient. Solid radionuclides suitable for use with a device 10 embodying features of the present invention are currently generally available as brachytherapy radiation sources (e.g., I-Plant.™ Med-Tec, Orange City, Iowa). Radiation may also be delivered by a device such as the x-ray tube of U.S. Pat. No. 6,319,188. The x-ray tubes are small, flexible and are believed to be capable of being maneuverable enough to reach the desired location within a patient's body.

The source delivery lumens of brachytherapy device 10 having features of the invention can be provided with a lubricious coating, such as a hydrophilic material. The lubricious coating preferably is applied to the elongate shaft 12 or to the cavity filling member, if one is present or both to reduce sticking and friction during insertion of a device 10. Hydrophilic coatings such as those provided by AST, Surmodics, TUA Systems, Hydromer, or STS Biopolymers are suitable.

A device 10 having features of the invention may also include an antimicrobial coating that covers all or a portion of the device 10 to minimize the risk of introducing of an infection during extended treatments. The antimicrobial coating preferably is comprised of silver ions impregnated into a hydrophilic carrier. Alternatively the silver ions are implanted onto the surface of the device 10 by ion beam deposition. The antimicrobial coating preferably is comprised of an antiseptic or disinfectant such as chlorhexadiene, benzyl chloride or other suitable biocompatible antimicrobial materials impregnated into hydrophilic coatings. Antimicrobial coatings such as those provided by Spire, AST, Algon, Surfacine, Ion Fusion, or Bacterin International would be suitable. Alternatively a cuff member covered with the antimicrobial coating is provided on the elongated shaft of the delivery device 10 at the point where the device 10 enters the skin.

Figure 9:
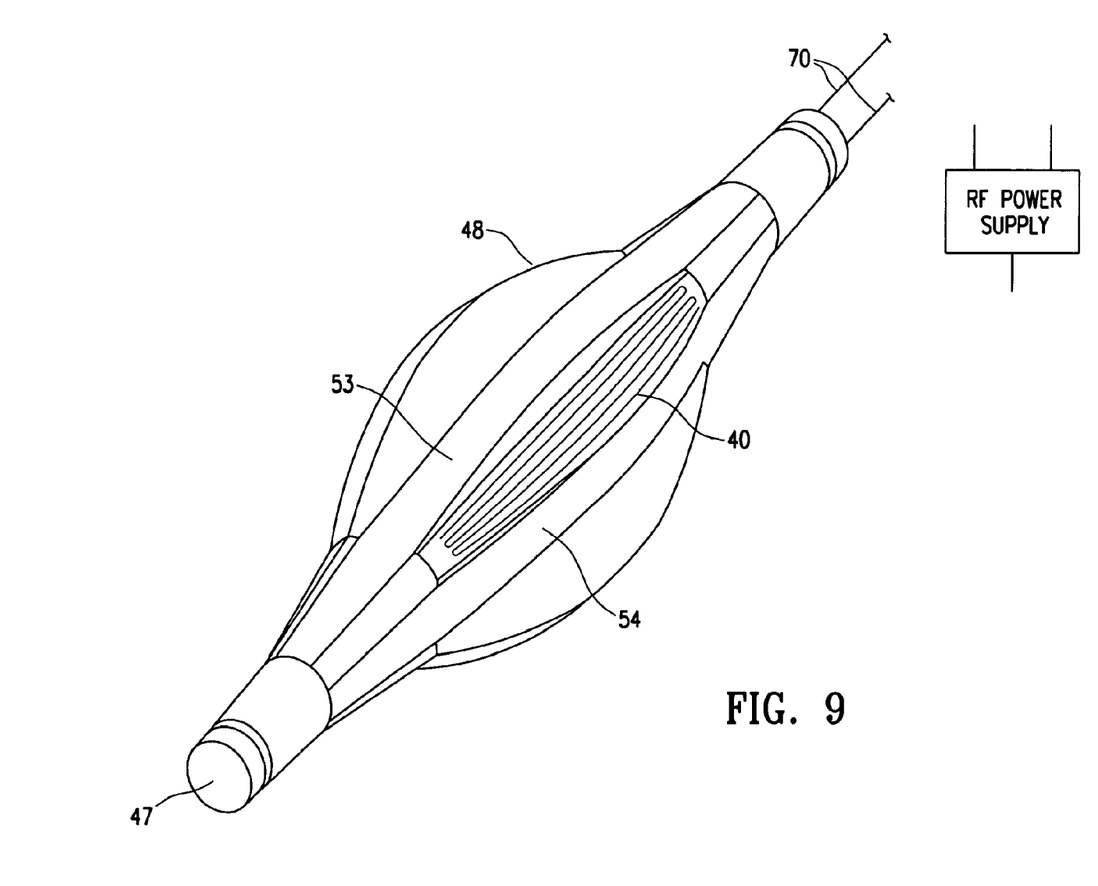
FIG. 9 is a perspective view of an alternative support member such as shown in FIG. 6 wherein the raised portions of the adjacent to the recess are provided with heating coils.

FIG. 9 illustrates a modified support member 48 which is provided with a heating coil 70 to raise the temperature of tissue in the cavity lining either simultaneously with or sequentially to irradiation of the cavity lining as previously described. While FIG. 9 depicts a heating 70 on one raised portion of the support member 48, a heating element may be provided on a plurality of raised portions of the support member. Preferably, the heating coils are powered by RF energy and are connected to a suitable high frequency generator. Voltage, current, frequency and duty factor may be adjusted to provide a suitable thermal treatment to tissue lining the cavity to augment the irradiation thereof. Other means may include heating the inflation fluid within the balloon 15. The heating of the inflation fluid may be exterior to the device 10.

While particular forms of the invention have been illustrated and described herein, it will be apparent that various modifications and improvements can be made to the invention. Additional details of the brachytherapy catheter devices may be found in the patents and applications incorporated herein. To the extent not otherwise disclosed herein, materials and structure may be of conventional design.

Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is therefore intended that this invention be defined by the scope of the appended claims as broadly as the prior art will permit.

Terms such as "element", "member", "component", "device", "means", "portion", "section", "steps" and words of similar import when used herein shall not be construed as invoking the provisions of 35 U.S.C. §112(6) unless the following claims expressly use the terms "means for" or "step for" followed by a particular function without reference to a specific structure or a specific action. All patents and all patent applications referred to above are hereby incorporated by reference in their entirety.

What is claimed is:

1. A brachytherapy device for irradiating tissue surrounding a body cavity within a patient, comprising:
   an elongated shaft having a inner lumen, a wall at least in part defining the inner lumen, a plurality of lumens within the wall and a central longitudinal axis;
   a distal shaft portion having a treatment location and a plurality of longitudinally separated wall segments, with at least one of the longitudinal wall segments having a lumen extending therein configured to receive a radiation source;
   a support member configured to support the plurality of longitudinally separated wall segments in off-set positions relative to the central longitudinal axis, wherein the support member has an inner lumen which is in fluid communication with the inner lumen defined by the wall of the elongated shaft; and
   a central tubular member received in the inner lumen of the elongated shaft and received in the inner lumen of the support member and configured to direct the radiation source through the support member to the treatment location.

2. The device of claim 1, wherein the distal shaft portion has a tip configured to engage distal ends of the wall segments.

3. The device of claim 2 wherein the tip is configured to seal the lumen extending within the at least one of the longitudinal wall segments.

4. The device of claim 2 wherein the tip is configured to seal the lumen configured to receive the radiation source.

5. The device of claim 1, wherein the distal shaft portion has an expandable member surrounding the treatment location configured to engage tissue of the body cavity and which has a contracted configuration and an expanded configuration spaced from at least one of the wall segments in the treatment location.

6. The device of claim 5 wherein the expandable member is a balloon with an interior configured to receive inflation fluid.

7. The device of claim 6 wherein at least one lumen of the plurality of lumens within the wall of the elongated shaft proximal to the distal shaft portion is configured to be in fluid communication with a source of inflation fluid and the interior of the balloon.

8. The device of claim 1, wherein the elongated shaft has at least one vacuum port which is in fluid communication with one of the plurality of lumens within the wall of the elongated shaft.

9. The device of claim 8 wherein the lumen in fluid communication with the vacuum port is configured to be in fluid communication with a vacuum source.

10. The device of claim 6 wherein the distal shaft portion has at least one vacuum port proximal or distal to the balloon that is in fluid communication with one of the plurality of lumens within the wall of the elongated shaft.

11. The device of claim 2 wherein the tip has at least one proximally extending plug element which is configured to be inserted into the lumen of the at least one of the longitudinal wall segments.

12. The device of claim 1, further comprising a heating element that is configured for connection to a high frequency electrical source, and configured to provide heat to tissue surrounding the cavity simultaneously with or sequentially to irradiation by the radiation source.

13. The device of claim 12 wherein the heating element heats inflation fluid within a balloon surrounding the treatment location.

14. The device of claim 12, wherein the heating element is provided with the support member.

15. The device of claim 1, wherein the support member has a plurality of recesses configured to receive the wall segments.

16. The device of claim 15, wherein the recesses of the support member are configured to support the wall segments in arcuate shapes.

* * * * *